US009316627B2

(12) United States Patent
Niiranen et al.

(10) Patent No.: US 9,316,627 B2
(45) Date of Patent: Apr. 19, 2016

(54) METHOD AND DEVICE FOR DETERMINING GAS COMPONENT INSIDE A TRANSPARENT CONTAINER

(71) Applicant: Oy Sparklike Ab, Espoo (FI)

(72) Inventors: Kai Niiranen, Jarvenpaa (FI); Miikkael Niemi, Espoo (FI); Mikko Syrjalahti, Espoo (FI)

(73) Assignee: OY SPARKLIKE AB, Helsinki (FI)

( * ) Notice: Subject to any disclaimer, the term of this patent is extended or adjusted under 35 U.S.C. 154(b) by 0 days.

(21) Appl. No.: 14/593,195

(22) Filed: Jan. 9, 2015

(65) Prior Publication Data

US 2015/0198499 A1 Jul. 16, 2015

Related U.S. Application Data

(60) Provisional application No. 61/927,539, filed on Jan. 15, 2014.

(51) Int. Cl.
| | |
|---|---|
| *G01N 21/55* | (2014.01) |
| *G01N 33/00* | (2006.01) |
| *G01M 3/00* | (2006.01) |
| *G01M 3/20* | (2006.01) |
| *G01M 3/22* | (2006.01) |
| *G01M 3/38* | (2006.01) |

(52) U.S. Cl.
CPC ........... *G01N 33/0006* (2013.01); *G01M 3/007* (2013.01); *G01M 3/207* (2013.01); *G01M 3/226* (2013.01); *G01M 3/38* (2013.01)

(58) Field of Classification Search
CPC ... G01N 21/553; G01N 21/55; G01N 21/554; G01N 21/474; G01N 21/57
USPC ......................................... 356/445
See application file for complete search history.

(56) References Cited

U.S. PATENT DOCUMENTS

| | | | | |
|---|---|---|---|---|
| 5,123,737 | A * | 6/1992 | Eichweber | G01S 17/42 356/152.3 |
| 6,545,749 | B1 * | 4/2003 | Andersson | G01C 3/08 356/4.01 |
| 2014/0063491 | A1 * | 3/2014 | Smith | G01J 1/00 356/123 |
| 2014/0204376 | A1 * | 7/2014 | Day | G01J 3/443 356/318 |
| 2014/0240691 | A1 * | 8/2014 | Mheen | G01S 17/89 356/4.07 |

FOREIGN PATENT DOCUMENTS

WO 2012156589 A1 11/2012

OTHER PUBLICATIONS

Paul L. Kebabian et al., "Determination of Argon-Filled Insulated Glass Window Seal Failure by Spectroscopic Detection of Oxygen", Institute of Physics Publishing, Measurement of Science and Technology vol. 14, 2003, pp. 983-988, Billerica, MA USA.

* cited by examiner

Primary Examiner — Tarifur Chowdhury
Assistant Examiner — Md M Rahman
(74) Attorney, Agent, or Firm — Young & Thompson

(57) ABSTRACT

A device for determining existence of a gas component inside a space of a glass unit includes detecting unit and calibration units. The detecting unit includes laser beam emitting elements emitting laser beam towards the space and detecting elements for detecting reflections of emitted laser beams. The calibration unit includes a calibration chamber having the same gas component as inside the space, and a reflector. The laser beam emitting and detecting elements are arranged to emit and receive beams at an angle so that the focus of the laser spot locates between the laser emitting and detecting elements and outside the line connecting them at the same position in relation to the detecting unit during the measuring process. The detecting and calibration units are movable in relation to each other for calibration purpose so that the laser beam travels through the chamber and the focus spot hits the reflector.

15 Claims, 2 Drawing Sheets

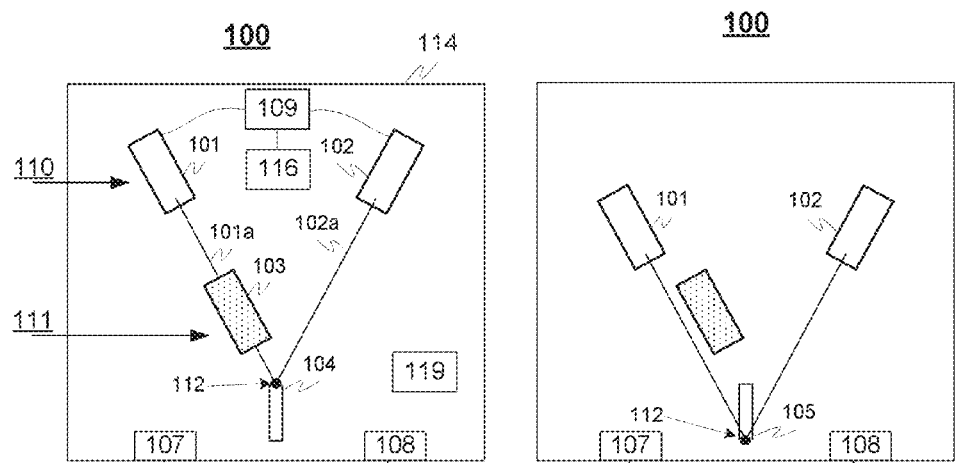
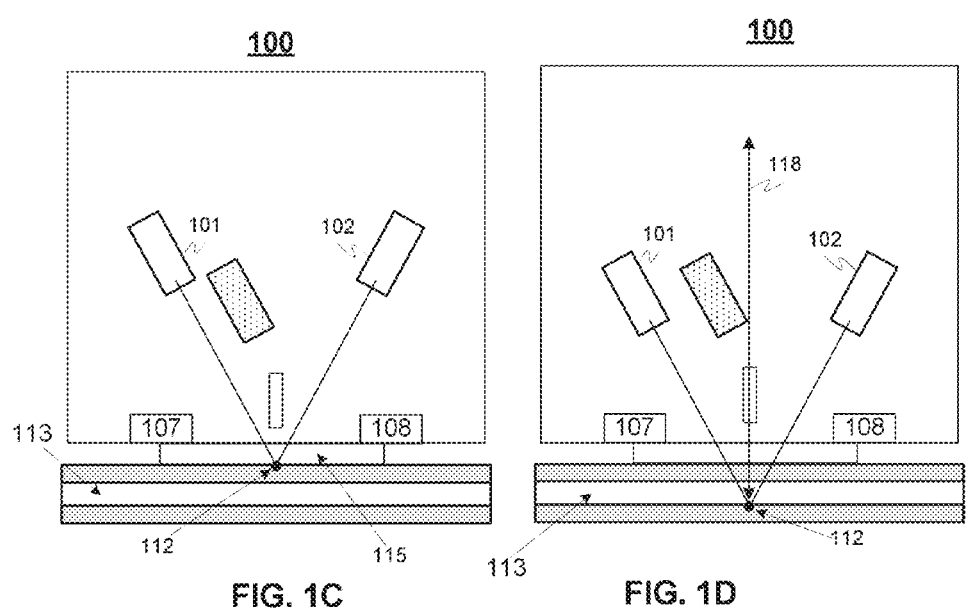

METHOD AND DEVICE FOR DETERMINING GAS COMPONENT INSIDE A TRANSPARENT CONTAINER

TECHNICAL FIELD OF THE INVENTION

The invention relates to a method and device for determining an interest gas component in particularly inside a glass unit of one or several separate cavities, such as insulating glass units, IGUs, or any other similar transparent container.

BACKGROUND OF THE INVENTION

In the glass manufacturing process glass sheets (known as float glass) can be combined with different kind of elements, such as coated or tempered layers to create glass panes for different purposes having specific properties. For example, insulating glass units, IGUs, are constructed typically with a configuration having two or more glass sheets with a closed space in between the sheets, where the closed space is filled with gas with low thermal conductivity, such as Argon, Xenon, Krypton Nitrogen or mixture of those. There is need in the industry to check the quality of the glass unit and ensure that there is no leakage, so that the filling gas has not leaked away.

Different kinds of solutions are known from the prior art for determining the quality and possible leakages of a gas mixture contained in the spacing. Typically these solutions are based on measuring concentration of the gas components in the gas mixture contained in the spacing, such as measuring absorption peak of the filling gases and thereby the concentration of the filling gas. However, the concentration measurements of the filling gas has some drawbacks, namely for different types of filling gas a different laser source must be used, which is clearly expensive and time consuming way to measure. Another drawback is that the gas volume inside the typical glass unit is very small, whereupon the amount of the gas to be measured is small and thereby also the absorption peak (amplitude of the peak) caused by said gas component to the measuring beam is very weak. In addition, and therefore, the location of the absorption peak of the gas component to be measured might be very hard to find from the measured signal due to environmental noise, which easily covers the absorption peak to be determined and thus makes the analysis very cumbersome and labour.

SUMMARY OF THE INVENTION

An object of the invention is to alleviate and eliminate the problems relating to the known prior art. Especially the object of the invention is to provide a method for performing a non-invasive determining of a quality of a glass unit or leakage of a gas component contained in a spacing of a glass unit or other transparent container or space. An additional object of the invention is to provide a method for determining any leakages of the gas components in each space separately at a same time, if the glass unit comprises a number of spaces.

The object of the invention can be achieved by the features of independent claims.

The invention relates to a device for non-invasively determining an existence gas component of interest inside a space and thereby any leakage of the space according to claim 1. In addition the invention relates to a corresponding method of claim 11.

According to an embodiment a device for non-invasively determining an existence of a gas component of interest inside a space comprises a detecting unit and a calibration unit. The detecting unit comprises a laser beam emitting means for emitting laser beam towards the space. In addition the detecting unit comprises a detecting means for detecting reflections of said emitted laser beams reflected from surfaces of the space. The measured space where the gas component is to be determined is typically a space of the insulating glass units, IGUs, where the space is closed by the glass sheets of the unit. Anyway the space might also be any other space or transparent container.

The calibration unit comprises at least one transparent chamber having at least the same gas component as to be determined and analysed inside the space. The gas component may be e.g. same as the filling gas, if the filling gas is measured. However, it is to be noted than in many case another gas than the filling gas is much easier to determine for leakages. Especially it is to be noted that if the glass unit has any leakage, the filling gas will leak away, but at the same time gas components of the surrounding air will diffuse or flow into the space of the glass unit. Thus the gas component to be measured and contained also in the calibration chamber might be e.g. $O_2$ or $CO_2$, as an example, and not necessarily the gas component of filling gas, such as Argon, Xenon, Krypton Nitrogen or mixture of those. If the measuring reveals the existing for example of Oxygen inside the glass unit, the leakage may be determined. According to an embodiment the calibration chamber may be filled with normal air having e.g. 21% of $O_2$. Again it is to be noted that a number of different chambers with different gas component can be used.

The laser beam emitting means and detecting means are arranged so to emit and receive beams advantageously in a fixed angle so that the focus of the laser spot locates between said laser emitting means and detecting means and outside the straight (virtual) line connecting said laser emitting means and detecting means. In addition the focus spot is configured to locate at the same position in relation to said detecting unit during the measuring and the calibration processes.

The detecting unit and a calibration unit are configured to be moved in relation to each other for a calibration purpose. In the calibration phase the laser beam is arranged to travel through the calibration chamber so that the focus spot hits a reflector of the calibration unit. The reflector may be a separate reflector, for example, and comprise a separate piece of glass. According to an embodiment it might also be a covering glass sheet (window, typically coated glass or quartz glass) of the device. In addition the detecting means is at the same time focused essentially to said focus spot and configured to image said reflected beam for analysing. The focusing of the detecting means (imaging only the focus spot) minimizes undesired optical interferences, which otherwise easily disturbs the measurements. The detecting means advantageously provides electrical signal corresponding an intensity of the reflected beam.

In the calibration process an electric feed current of the laser source is changed (WMS technique) in order to scan the peak location of the gas component to be determined. When starting the calibration process, the current is increased so to change the wavelength of the emitted laser beam. At the same time the current may be modulated by a sinusoidal signal in order to strengthen and make more reliable the signal to be determined. The current is increased to a certain limit so that the peak location caused by the absorption of the gas component to be measured is determined. Then the current is again decreased so to overlap the emitted wavelength of the laser source around the peak to be determined. Thus the peak location can be detected in the function of wavelength and/or the electric feed current of the laser source. As a result a peak pair is achieved.

It is to be noted that the measurement or determination existence of the interest gas component can be done even if only the location of peak is known and there is no need for calibrating the device so that to derive absolute concentration of the gas of interest. Thus the calibration should be understood as to seeking the locations of reference peak(s) of the gas component of interest. Typically the determination of the location of the peak is enough, especially if it is determined whether there is any leakage and if any environment gas has got inside the space. If there is leakage, only small signal at the location of said peak reveals the leakage and thus there is no need to know the absolute concentration of the measured gas component. Anyway it is to be also noted that if needed, the calibration may also be carry out so that the absolute concentrations can be measured. For this the different transparent containers with different concentration of the gas component inside these containers are measured in order to achieve different responses for different concentrations. Again the absolute concentration of the gas component inside the calibration chamber is not important, but it is used only the determining the location of the peak(s) of the gas to be measured.

For determination the detecting unit is configured to be moved towards and/or away said space for a determination purpose so that said focus spot sequentially hits the outer and inner surfaces closing said space, as well as travelling also through the space (at least when the reflection from the inner back surface is determined).

According to an embodiment the device comprises a hermetically sealed housing encapsulating the detecting unit and calibration unit. The housing is advantageously filled with a shielding gas, such as nitrogen or argon, for example. The filling gas is selected so that it is inert for the laser wavelength. The housing is additionally emptied essentially from the gas to be measured so that it would not interfere the measurement.

According to an embodiment the device is configured to perform a self-check advantageously before measurements. In the self-check the detecting unit is configured to perform the calibration and in addition to measure a volume inside the device housing so that the focus spot is configured to be reflected from a reflector so that the calibration chamber is not involved. If no signal is detected from said volume after calibration, there are no leakages and the housing and the shielding gas is working properly.

According to an embodiment the device is configured to change a temperature of the laser emitting means so to adjust the distance of the peak in the measured curve when scanning the wavelengths around the peak location of the gas component to be measured. By this the distance of the peaks can be changed in an advantageous position so that the peaks are not covering each other and that the best resolution is achieved. As an example the device may comprises a heating means, advantageously controllable heating means, such as a peltier element. The heating means is advantageously configured to manage temperature of the device and especially temperature of the laser emitting means, such as tunable diode laser.

In addition, according to an embodiment the device may also comprise an interfacing means, such as a sealing member, such as silicone sealing for example, which is configured to be introduced on the surface of the space of interest. In addition the device may comprise an underpressure providing means configured to provide underpressure in the volume between said device and the surface of the space defined by said interfacing means so to remove air between the device and the space, and to secure said device to said surface and thereby facilitating the positioning of the device e.g. essentially perpendicular to said surface and thereby minimizing measuring errors due to misaligned positioning. The device may also comprise a shielding gas providing means configured to provide shielding gas in the volume between said device and the surface of the space defined by said interfacing means and thereby remove any interfering gas components. Due to removing the air any possible interfering gas components are removed whereupon more accurate measuring results can be achieved.

Furthermore, according to an embodiment, the device may also be configured to determine the path length of the laser beam. This is advantageously implemented by measuring a distance of the focus spot and the angle said laser beam is emitted to the surface of the space (and reflected from the surface of the space). The distance of the focus spot from any reference line can be directly measured by the displacement of the detection unit, because the focus spot relates stationary in relation to said detection unit. According to an example e.g. step motor or the like can be used to move said detection unit, whereupon the output signal of the step motor can be construed to indicate the distance.

In the determination the detection unit is moved towards said space, whereupon the first reflections are achieved from the frontal and rear interfaces of the first surface when the focus spot reaches said interfaces. When the detection unit (and the focus spot) is moved further, the second reflections are caused by the frontal and rear interfaces of the second surface. When the space locates between the first and second surfaces, the signal (if any) of the gas to be measured is included in the measuring results of the beam reflected from the second surface (or more accurately its interfaces). Especially it is to be noted that the distance of the surfaces (or reflecting interfaces) can be determined based on the intensity maxima caused by said surfaces (or reflecting interfaces) and reading the displacement of the detection unit at the maxima, because the intensity maxima is reached when the focus spot hits said surfaces (or reflecting interfaces). When the distances of the different surfaces or interfaces are known the thickness of the surfaces (sheet layers) as well as thickness of the space can be simply calculated. Furthermore, when the angle of attack (and angle of reflection, is same as angle of incident beam) is known, the path length of the beam inside the space can be calculated using trigonometry.

The gas component in said spacing absorbs a very narrow-linewidth characteristic for each gas component, and the magnitude of the intensity variation due to absorption is proportional to the concentration of the gas. The intensity variations around or over the absorption line of the interest gas component is very non-linear. In the invention these non-linear variations in the intensity of the reflected or transmitted light beams around or over an absorption line of the interest gas component is then determined for determining the concentration of the gas component.

According to an embodiment also an additional reflector can be used at the opposite side of the glass unit as a surface or interface reflecting the focus spot back through the glass unit on the detector. When using the reflector the intensity of the reflection is typically more intensively than the reflection from any other surfaces.

The absorption signal to be detected in measurements and calibration is advantageously manipulated by WMS or FMS technique, such as by scanning a sinusoidally frequency-modulated diode laser over the absorption feature of the gas component to be determined in order to strengthen the second order polynomial fitted to the non-linear curve representing the variation in the intensity of the detected beams and concentration of the gas component to be detected and/or to minimize the low-frequency noise induced.

The performance of direct absorption is often degraded by the occurrence of 1/f noise. A common way to avoid such low frequency noise of system components, for example 1/f laser excess noise, is to shift the absorption signal to a higher frequency. In TDLAS technique, this can be achieved by a modulation of the diode laser operation current. Such modulation results in a modulation of the instantaneous laser frequency. Upon interaction with the non-linear reflected intensity profile of an absorption line, this will result in a periodic modulation of the detected intensity. This allows detection of absorption signal at the fundamental modulation frequency or its overtones.

For example a sinusoidal modulation of the diode laser operation current results in a sinusoidal wavelength (and amplitude) modulation of the laser output. Interaction with a wavelength-dependent and non-linear reflection signal (e.g. absorption lineshape) results in a periodic, but non-sinusoidal, reflection signal that consists of the modulation frequency itself as well as its harmonic overtones. This can be used in an embodiment to shift the detection frequency to the high frequency region less affected by low frequency noise (e.g. 1/f noise), and thus improving the sensitivity. This is typically achieved by letting a lock-in amplifier measure the amplitude of the harmonic components (most commonly, the second) as the laser is tuned over an absorption line of interest.

The invention offers many advantageous features over the known prior art methods, such as easy internal calibration process even before every measurements. In addition according to the invention it is possible to compensate inaccuracies due to temperature adjustment of the laser source affecting to the wavelength of the laser emitted beam and this to measuring data. In addition the invention enables the determinations and measurements even without any accurate knowledge of the concentration of the gas component used in calibration, because essentially only the location(s) of the peak to be measured matters. Furthermore the device of the invention is very reliable, because of the self-check. The calibration process as well as the self-check may be performed automatically and fast even before every measurement.

BRIEF DESCRIPTION OF THE DRAWINGS

Next the invention will be described in greater detail with reference to exemplary embodiments in accordance with the accompanying drawings, in which:

FIGS. 1A-1D illustrates principles of exemplary device according to an advantageous embodiment of the invention.

DETAILED DESCRIPTION

Figure 2:
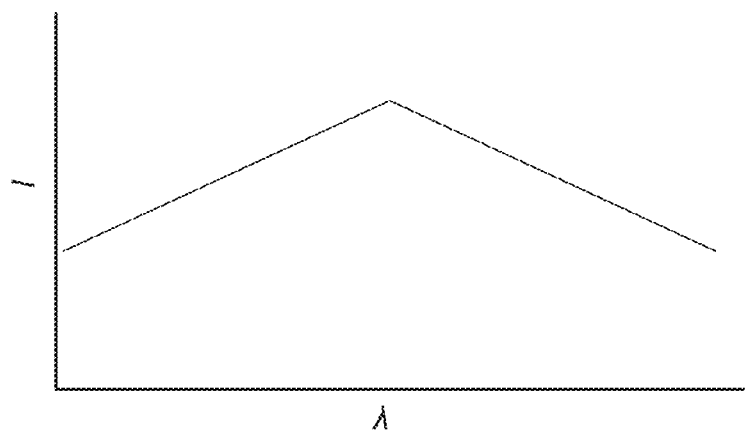
FIG. 2 illustrates exemplary principles of a calibration and measuring methods according to an advantageous embodiment of the invention.

FIGS. 1A-1D illustrates principles of exemplary device 100 according to an advantageous embodiment of the invention, wherein the device comprises a detecting unit 110 and a calibration unit 111. The detecting unit 110 comprises a laser beam emitting means 101, such as laser source, and a detecting means 102. In addition the detecting unit 110 unit advantageously comprises suitable optical means (not shown) focusing the emitted beam 101a to a certain focus spot 112, as well as to focus said detection means to said focus spot 112.

The calibration unit 111 comprises at least one transparent chamber 103 having at least the same gas component as to be determined and analysed inside the space 113.

The laser beam emitting means and detecting means (advantageously with the help of suitable optical means, such as lenses (not shown)) are arranged so to emit and receive beams advantageously in a fixed angle so that the focus of the laser spot locates 112 between said laser emitting means 101 and detecting means 102 and outside the straight (virtual) line connecting said laser emitting means and detecting means, such as below the line as is the case in FIGS. 1A-1D. In addition the focus spot 112 is configured to locate at the same position in relation to (at the same distance from) said detecting unit 110 during the measuring and the calibration processes, as can be seen in different calibration and measuring phases of FIGS. 1A-1D.

In FIG. 1A the detecting unit is moved (lowered) for a calibration purpose. In the calibration phase the laser beam 101a is arranged to travel through the calibration chamber 103 so that the focus spot 112 hits a reflector 104 of the calibration unit. The reflector may be a separate reflector, for example, and comprise a separate piece of glass. The detecting means 102 is at the same time focused essentially to said focus spot 112 and configured to image only said reflected beam 102a for analysing.

Also a self-check may be done, where a volume inside the device housing 114 is measured, as is illustrated in FIG. 1B. In the self-check the focus spot 112 is configured to be reflected from a reflector 105 so that the calibration chamber 103 is not involved in the measurement. If no signal is detected from said volume, there are no leakages and the housing and the shielding gas inside the housing is working properly. Advantageously the housing is a hermetically sealed housing encapsulating the detecting unit 110 and calibration unit 111.

For determination the detecting unit is configured to be further moved towards and/or away of the space 113 for a determination purpose, as can be seen in FIGS. 1C and 1D. There the focus spot 112 sequentially hits the different surfaces closing said space 113. When reflecting from the back surface (FIG. 1D), the beam 101a, 102a travels also through the space 113, whereupon the absorption of the gas of interest can be detected and thereby any leakage of the unit revealed.

The device may also comprise an interfacing means 106, such as a sealing member, such as silicone sealing for example, which is configured to be introduced on the surface of the space 113 of interest. In addition the device may comprise an underpressure providing means 107, such as a vacuum pump, configured to provide underpressure in the volume 115 between said device 100 and the surface of the space 113 so to remove interfering air from the volume, as well as to secure the device to said surface and thereby facilitating the positioning of the device e.g. essentially perpendicular to said surface and thereby minimizing measuring errors due to misaligned positioning. The device may also comprise a shielding gas providing means 108 configured to provide shielding gas in the volume 115 and thereby remove any interfering gas components.

Figure 3:
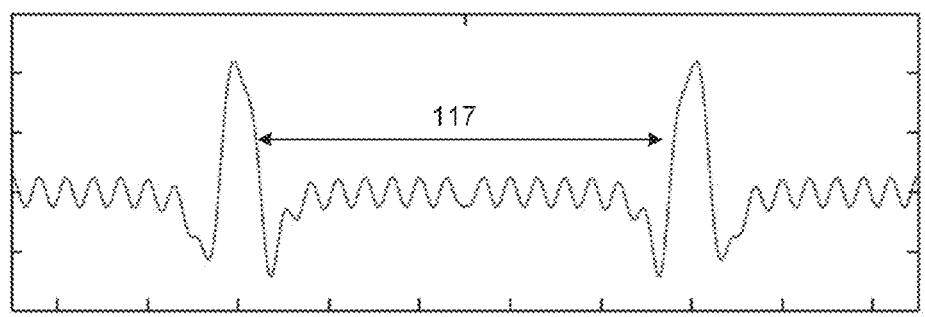
FIG. 3 illustrates exemplary measured curve according to an advantageous embodiment of the invention.

In addition the device may comprise controlling means 109 for controlling the operation of the device, such as movements of the detection unit 110, and the operation of the laser beam emitting means 101. As an example the controlling means 109 may control the electric current of the laser source 101 so to scan the wavelength area around the gas of interest. In the calibration process as well as also in determination process the current is changed, as can be seen in the curvature of FIG. 2, where the wavelength of the emitted beams are changed in the function of feed electric current of the laser source. FIG. 3 illustrates a measured curve, where the peak induced by the gas of interest can be found essentially at the same wavelength. These locations of peak (wavelength, or in practice the electric current of the laser source enabling said wavelength) is then used in determination of the gas of interest in said space 113.

Furthermore the device may also comprise temperature managing means 116, such as a peltier element, which is configured to change a temperature of the laser emitting means 101. By changing the temperature the distance 117 of the peaks in the measured curve can be adjusted when scanning the wavelengths around the peak location.

The distance (displacement) 118 of the focus spot 112 can be easily determined when said detecting unit is moved. The device may also comprise data processing unit 119, which is configured to perform any calculations and determinations of the measured intensities, as well as the path length of the beams and order of interfaces or surfaces caused the reflections of the beam. In addition the data processing unit 119 may be configured to determine possible existence of the gas of interest inside the measured space and thereby also any possible leakages, and correspondingly to perform any indication of leakage, such as an alarm.

The invention has been explained above with reference to the aforementioned embodiments, and several advantages of the invention have been demonstrated. It is clear that the invention is not only restricted to these embodiments, but comprises all possible embodiments within the spirit and scope of the inventive thought and the following patent claims. Even though only a glass unit is described above, it is to be noted that different kinds of reflective transparent objects can be determined, such as for example a glass or plastic, such as float glass, laminated glass, toughened or tempered glass, especially an insulating glass or glass coated with a coating, for instance an electrically conductive coating, as well as also other transparent containers.

The invention claimed is:

1. A device for non-invasively determining existence of a gas component of interest inside a space of a glass unit, wherein the device comprises a detecting unit and a calibration unit, wherein said detecting unit comprises a laser beam emitting means emitting laser beam towards said space and detecting means for detecting reflections of said emitted laser beams reflected from said space, wherein
   the calibration unit comprises at least a transparent calibration chamber having same gas component as to be determined inside the space, and a reflector,
   the laser beam emitting means and detecting means are arranged so to emit and receive beams in an angle so that the focus of the laser spot locates between said laser emitting means and detecting means and outside the line connecting said laser emitting means and detecting means at the same position in relation to said detecting unit during the measuring process,
   wherein
   said detecting unit and a calibration unit are configured to be moved in relation to each other for a calibration purpose so that said laser beam travels through said chamber and the focus spot hits the reflector of the calibration unit, whereupon the detecting means is focused essentially to said focus spot and configured to image said reflected beam, and
   said detecting unit is configured to be moved towards and/or away said space for a determining purpose of the existence of the interest gas component so that said focus spot sequentially hits the surfaces or interfaces of the said space.

2. A device of claim 1, wherein the device comprises a hermetically sealed housing encapsulating said detecting unit and calibration unit, said housing being filled with shielding gas being inert for the laser wavelength and emptied essentially from the gas to be measured.

3. A device of claim 1, wherein said device is configured to perform a self-check, where said detecting unit is configured to perform said calibration and in addition to measure a volume inside said device housing so that the focus spot is configured to be reflected from a reflector so that said calibration chamber is not involved.

4. A device of claim 1, wherein the device is configured to change an electric current of the laser source in order to scan the wavelengths around the assumed peak of the gas component to be determined in calibration process in order to determine accurate location of said peak in the function of electric feed current of the laser emitting means, whereupon the device is configured to use said wavelengths or peak locations also in measuring process for determining the gas component inside the space.

5. A device of claim 1, wherein the device is configured to change a temperature of the laser emitting means so to adjust the distance of the peak in the measured curve when scanning the wavelengths around the peak location of the gas component to be measured.

6. A device of claim 1, wherein the device comprises interfacing means configured to be introduced on the surface of the space to be measured, and an underpressure providing means configured to provide underpressure in the volume between said device and the surface of the space defined by said interfacing means.

7. A device of claim 1, wherein the device comprises interfacing means configured to be introduced on the surface of the space to be measured, and a shielding gas providing means configured to provide shielding gas in the volume between said device and the surface of the space defined by said interfacing means.

8. A device of claim 1, wherein the device is configured to determine the path length of the laser beam based on said distance of the focus spot and the angle said laser beam is emitted to the surface of the space.

9. A device of claim 1, wherein said laser beam emitting means and detecting means are arranged so to emit and receive said beams at fixed angle so that the mutual angle of the incident and reflected beams remains constant and the focus spot remains stationary in relation to said detecting unit when moving said the detecting unit towards and away said space.

10. A device of claim 1, wherein the device comprises a heating means, such as a peltier element, configured to manage temperature of the device and especially temperature of the laser emitting means, such as tunable diode laser.

11. A method for non-invasively determining existence of a gas component of interest inside a space, wherein in the method a laser beam is emitted towards said space and reflections from said space are detected, wherein
   the laser beams are emitted and reflected beams are received in an angle so that the focus of the laser spot locates between said laser emitting means and detecting means and outside the line connecting laser emitting means and detecting means at the same position during the measuring process in relation to a detecting unit comprising said laser emitting means and detecting means, wherein
the detecting unit and a calibration unit are moved in relation to each other for a calibration purpose so that said laser beam travels through a transparent calibration chamber of the calibration unit and the focus spot hits the reflector of the calibration unit, whereupon the detecting means is focused essentially to said focus spot and images said reflected beam, wherein the calibration chamber comprises same gas component as to be determined inside the space and moving the detecting unit towards and/or away said space for a determining purpose of the existence of the interest gas component so that said focus spot sequentially hits the surfaces or interfaces of the said space.

12. A method of claim 11, wherein a self-check is performed, where said detecting unit is performing said calibration process and in addition measures a volume inside the device housing so that the focus spot is reflected from a reflector so that said calibration chamber is not involved in the measurement.

13. A method of claim 11, wherein an electric current of the laser source is changed in order to scan the wavelengths around the assumed peak of the gas component to be determined in calibration process in order to determine accurate location of said peak in the function of electric feed current of the laser emitting means, and whereupon said wavelengths or peak locations are used also in determining process for determining the gas component inside the space.

14. A method of claim 11, wherein a temperature of the laser emitting means is manipulated so to adjust the distance of the peak in the measured curve when scanning the wavelengths around the peak location of the gas component to be measured.

15. A method of claim 11, wherein an interfacing means is introduced on the surface of the space to be measured, and an underpressure is provided into the volume between said device and the surface of the space defined by said interfacing means and/or wherein shielding gas is provided into the volume between said device and the surface of the space defined by said interfacing means.

* * * * *